United States Patent [19]

Ooe et al.

[11] Patent Number: 4,690,147

[45] Date of Patent: Sep. 1, 1987

[54] METHOD AND APPARATUS FOR MEASURING GAS PARTIAL PRESSURE IN LIVING BODY

[75] Inventors: Akihiko Ooe, Komaki; Tetsuo Imaiida; Teruyoshi Uchida, both of Nagoya; Hirotaka Kojima, Kasugai, all of Japan

[73] Assignee: Mitsubishi Rayon Co., Ltd., Tokyo, Japan

[21] Appl. No.: 815,760

[22] Filed: Jan. 2, 1986

Related U.S. Application Data

[63] Continuation of Ser. No. 486,413, Apr. 19, 1983, abandoned.

[51] Int. Cl.⁴ ............................................. A61B 5/00
[52] U.S. Cl. .................................. 128/635; 204/403; 204/408
[58] Field of Search ................. 128/635; 204/408, 403

[56] References Cited

U.S. PATENT DOCUMENTS

| | | | |
|---|---|---|---|
| 3,710,778 | 1/1973 | Cornelius | 128/635 |
| 4,176,031 | 11/1979 | Rosenblum | 204/408 X |
| 4,269,194 | 5/1981 | Rayburn | 128/635 X |
| 4,301,807 | 11/1981 | Mentelos | 128/635 |
| 4,384,586 | 5/1983 | Christiensen | 128/635 |
| 4,431,004 | 2/1984 | Bessman et al. | 128/635 |
| 4,442,841 | 4/1984 | Uehara et al. | 128/635 |

OTHER PUBLICATIONS

Brown et al, "A Unique Electrode Catheter . . . ", *Oxygen Transport to Tissue*, pp. 1103–1108, 1973.

*Primary Examiner*—Lee S. Cohen
*Attorney, Agent, or Firm*—Ladas & Parry

[57] ABSTRACT

A method and apparatus for measuring a gas partial pressure in a living body on the basis of the principle of polarography. A gas partial pressure sensor includes a biomedical electrode inserted in the living body. A temperature sensor is further provided to measure a temperature of the living body. A polarographic current value measured by the gas partial pressure sensor is corrected to a current value at a reference temperature depending on the temperature measured by the temperature sensor. Then the gas partial pressure at the reference temperature is determined based on a working curve which represents a relationship between the corrected polarographic current value and the gas partial pressure at the reference temperature.

9 Claims, 4 Drawing Figures

METHOD AND APPARATUS FOR MEASURING GAS PARTIAL PRESSURE IN LIVING BODY

This is a continuation of co-pending application Ser. No. 486,413 filed on Apr. 19, 1983, now abandoned.

This invention relates to a method and apparatus for measuring the concentration of various kinds of gases existing in biological tissue and biological fluid, especially, blood, the method being one of measures adapted for quantitatively gathering biological conditions in the field of medical science. In particular, the present invention relates to a method and apparatus for measuring a partial pressure in a living body on the basis of the polarography.

Two major methods have hitherto been available for the gas concentration or partial pressure measurements.

A first method is based on the so-called spot measurement wherein blood is extracted from a living body and thereafter the gas concentration is measured through a chemical analysis process.

A second method is such that a small sensor is inserted into a living body and the gas concentration in terms of an electrical signal is measured.

Disadvantageously, the first method consumes much time until a result is obtained and besides, blood being in process of extraction from the living body tends to come into contact with ambient air, and gas exchange will be caused between the extracted blood and the ambient air with the result that a measured value representative of a gas concentration in the living body tends to be inaccurate.

The second method, on the other hand, is excellent which can provide instantaneous results, thus facilitating on-line monitoring of a living body condition. This method has therefore been proposed in various ways mainly on the basis of polarographic process. This method utilizing an electrode reaction, however, faces a problem of temperature dependency in which current or voltage values obtained greatly depend on temperatures and accurate values can not be obtained unless the living body is kept at a constant temperature.

For example, a sensor for measuring the oxygen concentration in liquid usually has a cathode made of a noble metal such as gold, platinum, silver or the like and an anode, such as an Ag/AgCl electrode. Oxygen is reduced at the surface of the cathode and a polarographic current which has a small current value due to the reducing reaction is measured. Since the current value varies with an oxygen concentration in the liquid and temperature of the liquid as well, it can not be concluded that a varying current value directly indicates a variation in the oxygen concentration in the liquid. Accordingly, in order to determine the variation in the oxygen concentration in the liquid, the liquid must be kept at a constant temperature or the oxygen concentration must be corrected by measuring temperature changes so as to be converted into a value at a reference temperature.

With an object to be examined in the form of a living body, however, it is practically difficult to maintain the living body at a constant temperature and such a maintenance is contradictory to the very purpose of on-line monitoring of the living body. For these reasons, appropriate temperature correction is required.

Further, in measuring a partial pressure of gas prevailing in blood with an electrode made of noble metal alone, measured values vary on account of pulsation or lowered reaction rate by blood component deposition on the electrode surface. To cope with such problems, it has been proposed to apply various coverings or coatings on the electrode surface. Since in this case the covering or coating by itself increases the temperature dependency, the need for temperature correction becomes imminent more and more.

It is an object of the present invention to provide a method and apparatus which provide accurate and rapid measurements of a gas partial pressure in a living body on the basis of the polarography principle by compensating for temperature changes in the living body.

According to the invention, a gas partial pressure sensor having a biomedical electrode disposed in the living body and a separate temperature sensor are disposed in or on the living body, an output value produced from the gas partial pressure sensor is sequentially corrected to a value at a reference temperature by a body temperature information signal produced from the temperature sensor in accordance with a predetermined temperature correction formula, and the gas partial pressure value is sequentially calculated from a predetermined working curve which represents a relationship between the gas partial pressure value and the corrected output value from the gas partial pressure sensor, both values being at the reference temperature.

The gas partial pressure in the living body is usually represented by a value at a reference temperature of about 37° C. But, sometimes the bodily temperature decreases by scores of centigrade degrees during a surgical operation. Especially, during an operation for heart disease, the body is sometimes cooled to below 10° C. After the operation, the patient often becomes feverish with his temperature rising to over 40° C. Thus, the body temperature deviates from the reference temperature by over 10° C. during the operation and by 5 to 6° C. after the operation. Even with the dropping mercury electrode described previously, the electrolytic current varies by 2% as the temperature varies by 1° C. and with the electrode used in the present invention, the electrolytic current varies by about 3%. For example, when the temperature of the living body deviates from the reference temperature by 20° C., the electrolytic current deviates from the actual value by 40 to 60%. Accordingly, without the correction according to the present invention, the measured value of the partial pressure in the living body greatly differs from an actual partial pressure. Conversely, the method of the present invention can reduce the error to a large extent to assure accurate measurement of actual gas partial pressure and can constantly apprize physicians and nurses of an accurate partial pressure in blood or tissue of the patient.

The invention will now be described by way of example with reference to the accompanying drawings.

Figure 1:
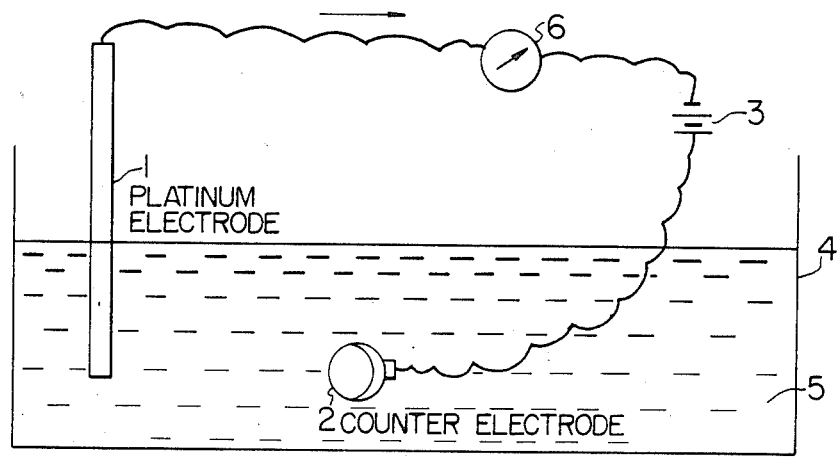
FIG. 1 is a diagram useful in explaining the principle of polarography.

Referring to FIG. 1, when a voltage is applied across a cathode, or platinum electrode 1 which constitutes a biomedical electrode, and an anode, or counter electrode 2 in a solution 5 in a container from a power supply 3, a polarographic current I due to electrolytic reaction flows and indicated by a meter 6. With a dropping mercury electrode, for example, the current I varies under the influence of a temperature dependency because of the gas diffusion by about 2% at 1° C. In other words, the amount of the temperature dependency is about 2%/°C.

Figure 2:
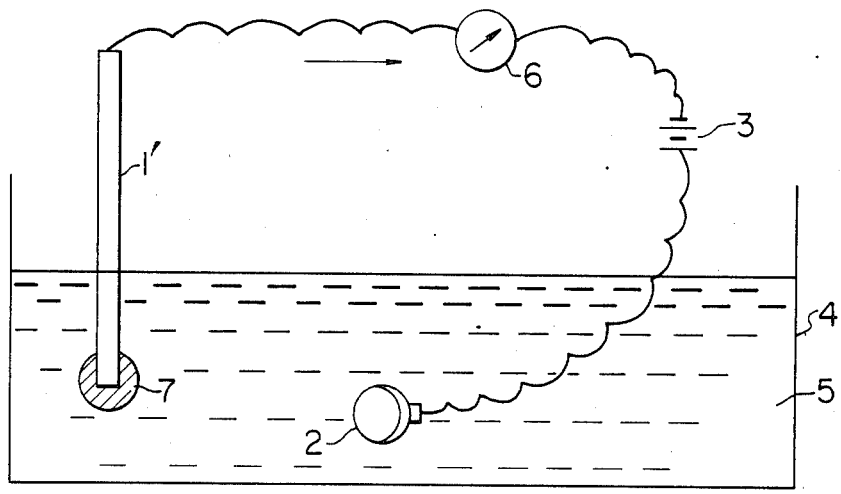
FIG. 2 is another diagram similar to FIG. 1 in which a platinum electrode has a porous membrane as a covering.

It has been proposed as shown in FIG. 2 to use a biomedical electrode 1' whose tip end surface is covered with a membrane which has an outer thin, dense layer having fine pores of an average diameter which is greater than 0.01 μm and is preferably 20 Å to 0.7 μm and an inner porous layer, contiguous to and integral with the outer layer, having fine pores of an average diameter of 0.7 μm or more, in U.S. patent application Ser. No. 259,112 and European patent application No. 81/301723.31 assigned to the same assignee as the present application. When the electrode 1' having its tip end covered with such a porous membrane 7 is used, the temperature dependency is larger than that of the dropping mercury electrode since many factors such as pore size, surface affinity and thickness of the porous membrane 7 affect the gas diffusion to increase the temperature dependency, thereby adversely affecting the gas partial pressure measurement. Through various experiments, the present inventors found that the polarographic current I was in a certain relationship with temperatures of an object to be examined, and that temperature correction for the polarographic current can be accomplished by using this relationship.

Figure 3:
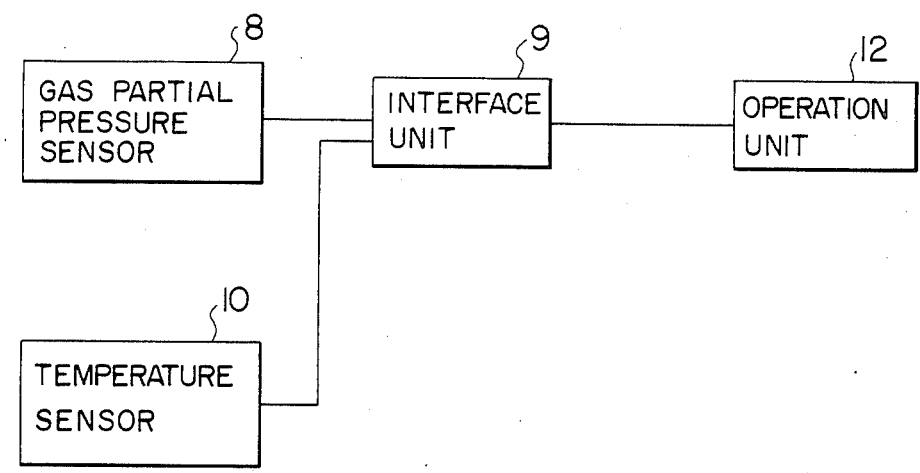
FIG. 3 is a circuit block diagram of the apparatus according to the present invention.

FIG. 3 is a block diagram for implementation of the present invention. In this embodiment, in order to eliminate the problems described previously, an operation unit 12 comprise a microcomputer board so that a value of a polarographic current I from a gas partial pressure sensor 8 is digitized by an interface unit 9 and inputted to the operation unit 12 and a biomedical temperature information signal from a temperature sensor 10 is digitized by the interface unit 9 and inputted to the operation unit 12, and the polarographic current value is temperature corrected and calculated from a predetermined value and a programmed formula to provide a gas partial pressure value. The same results may be obtained by an operation unit 12 of a mini-computer or of a dedicated logical circuit which substitutes for the microcomputer operation unit 12. A subsidiary advantage of the present invention resides in that in addition to the input data for a working curve preparation which is programmed in advance of measurement, a new value can be readily inputted at a desired time.

More particularly, in accordance with the principle of polarography, the output signal of the partial pressure sensor developing in the course of time lapse varies with not only temperatures but also, for example, amounts of substance in blood component deposited to the platinum electrode, or biomedical electrode as described previously, and variations in the sensor output signal can not be eliminated completely even when the porous membrane 7 is applied to the platinum electrode 1'. Accordingly, it is very advantageous that a new value for the working curve preparation can be inputted in an advanced phase of the measurement.

Correction procedures will now be described specifically.

As far as the principle of polarography is concerned, the linear relation, as represented by $$P = aI + b \tag{1}$$

where P is the gas partial pressure, I is the polarographic current value and a and b are constants, is held between the polarographic current value I and the gas partial pressure P. Accordingly, the gas partial pressure can be determined by measuring the polarographic current value whenever constants a and b are determined in advance. In this manner, a working current which represents the equation (1) can be prepared.

The polarographic current I has a temperature dependency as described previously. The present inventors have studied the temperature dependency in various manners to find that the following equation holds approximately between the current value and the temperature:

$$I_t = I_{sT} k^{T-t} \tag{2}$$

where $I_t$ is the polarographic current value at a temperature t, $I_{sT}$ is the polarographic value at a reference temperature T, and k is the temperature coefficient. The temperature coefficient k is specific to the gas partial pressure sensor but sensors produced under the same condition have substantially the same temperature coefficient. For precise measurement, however, several kinds of solutions having known gas partial pressure values are prepared, and currents and temperatures are measured for the respective kinds of solutions at different temperatures so that a temperature coefficient specific to a sensor participating in the measurement can be obtained through a method of least squares. For example, gas partial pressure sensors with platinum electrodes covered with the aforementioned porous membrane which were produced in the same lot under a certain condition had an average temperature coefficient k of 0.97 with a variation of ±0.01. It follows therefore that if the manufacture condition is monitored and controlled properly, the temperature coefficient will satisfactorily be regarded as being constant for the purpose of the measurement.

Next, the relationship between gas partial pressure and current value, i.e., the working curve can be determined in various manners as itemized below.

(i) A biomedical electrode of a gas partial pressure sensor is placed in an object to be measured and a temperature sensor is placed in or on the object to be measured. The working curve is then determined from a current value I and a temperature t at this time, and a gas partial pressure value $P_{sT}$ in the object measured by using a separate instrument such as for example a commercially available batch type oxygen partial pressure measuring instrument, and a residual current value $I_o$ (current value for a gas partial pressure of zero) of the gas partial pressure sensor as well. More particularly, a current value $I_{sT}$ at a reference temperature T° C. is determined from a current value $I_t$ measured at a temperature t° C. in accordance with equation (2).

The corrected current value $I_{sT}$ thus determined is related to the gas partial pressure $P_{sT}$ in accordance with the equation (1). The constant a in the equation (1) representative of a gradient of the current value relative to the gas partial pressure is $P_{sT}/(I_{sT}-I_o)$, and the constant b which is $P-aI$ is determined by substituting $P_{sT}$, $P_{St}/(I_{sT}-I_o)$, and $I_{sT}$ for P, a and I, respectively, in equation (1).

(ii) A gas partial pressure sensor and a temperature measuring sensor are placed in one kind of solution having a known gas partial pressure value $P_{sT}$. The working curve is then determined from current value I, temperature t, gas partial pressure value P and residual current $I_o$ of the gas partial pressure sensor at this condition. Subsequently, constants a and b are determined as in item (i).

(iii) A gas partial pressure sensor and a temperature sensor are placed in two kinds of solutions having known gas partial pressure values, and the working curve is determined from current values $I_1$ and $I_2$, temperatures $t_1$ and $t_2$, and gas partial pressure values $P_1$ and $P_2$ for the different kinds of solutions in those conditions. In particular, the current value $I_1$ for one solution and the current value $I_2$ for the other solution are respectively converted into current values at the reference temperature T° C. as in items (i) and (ii) and the constants a and b in the equation (1) are determined in a similar manner.

The gas partial pressure P can be determined from the polarographic current value I in accordance with the equation (1), by using the constants a and b obtained through any one of methods itemized in (i), (ii) and (iii) as above.

The residual current $I_o$ in (i) and (ii) methods is specific to the gas partial pressure sensor. However, the present inventors have found that sensors produced under the same condition have substantially the same value of residual current in terms of a converted gas partial pressure, as well as the temperature coefficient k. For example, gas partial pressure sensors with platinum electrodes (biomedical electrodes) covered with the aforementioned prorous membrane have a residual current which corresponds to an oxygen gas partial pressure of about 2 mmHg. As a result, the value of 2 mmHg may be used as the value of b instead of measuring the residual current $I_o$. The solution having a known gas partial pressure is required to contain electrolytic ions and preferably, it is physiological saline solution or blood.

The operator can select at will one of the above three methods. A fixed value of the temperature coefficient k is inputted in advance but for precise measurement, the operator may input a value of the temperature coefficient k specified to a sensor used.

An arrangement for implementing the present invention will now be described with reference to FIG. 4.

Figure 4:
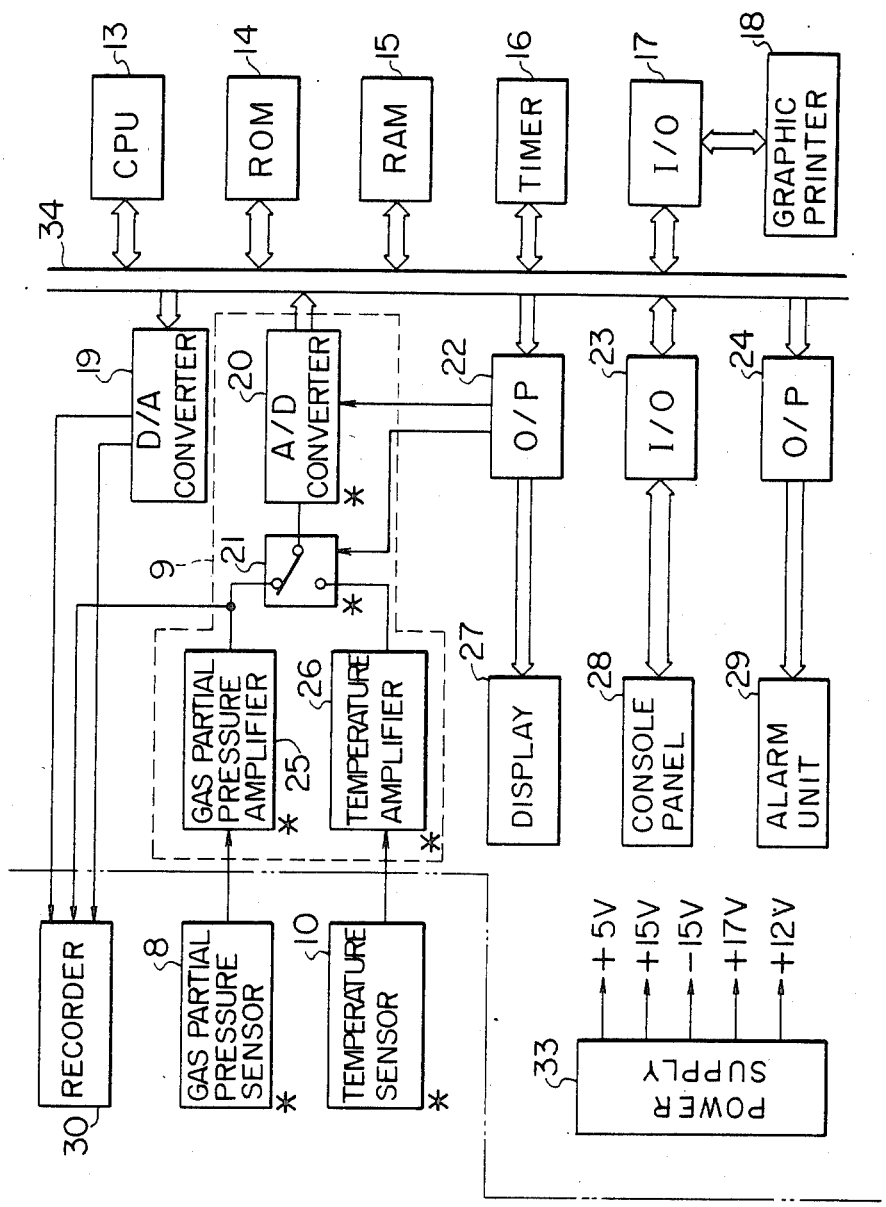
FIG. 4 is a detailed block diagram of the apparatus according to the present invention.

In FIG. 4, an output signal from a gas partial pressure sensor 8 is amplified suitably by a partial pressure amplifier 25 and transferred to a CPU bus line 34 via a remote switch 21 and an A/D converter 20. Connected to the CPU bus line 34 are a CPU 13, a ROM 14, a RAM 15, a timer 16 and various I/O and O/P boards 17, 22, 23 and 24.

The output signal from the gas partial pressure sensor 8 transferred to the CPU bus 34 is stored in a pertinent area of the RAM 15 in accordance with a program which has been stored in the ROM 14 and by the action of the CPU 13. On the toher hand, the output signal from the temperature sensor 10 is transferred to the CPU 13 via a temperature amplifier 26, the remote switch 21, the A/D converter 20 and CPU bus 34. The remote switch 21 is changed over at a suitable interval by a command via an O/P 22 in accordance with the program, for example, an interval of 200 to 1000 msec in a measurement of a partial pressure of oxygen in blood, and an interval of 5 to 10 sec in a measurement of a partial pressure in tissue in a living body, since in these cases generally, there is no need to recognize extremely rapid changes in the partial pressure and temperature.

As a result, the output signals from the gas partial pressure sensor 8 and temperature sensor 10 are alternately and intermittently transferred to the CPU 13 depending on the interval of the change over of the remote switch 21.

In the CPU 13, a polarographic current value $I_t$ represented by the output signal of the gas partial pressure sensor 8 is corrected to a current value $I_{ST}$ at a reference temperature T as described in the foregoing, and then a gas partial pressure P at the reference temperature T is calculated on the basis of the corrected current value $I_{ST}$ and the working curve. The resultant gas partial pressure P calculated sequentially, or rather practically almost continuously, is displayed on a display 27 numerically and is recorded graphically and numerically on a graphic printer 18, together with the temperature value or the gas partial pressure alone.

An extension line may also be provided for delivery of the data to an ordinary analog recorder 30 where the recorder 30 is additionally used.

A console panel 28 includes a plurality of console panel switches adapted to input data for preparing the working curve before or during the calculation of the gas partial pressure and to input the operator instructions in order to effect an accurate and updated correction. The console panel 28 further includes pilot lamps (not shown) adapted to confirm or monitor the operations in progress.

The one series of data input system illustrated herein may be modified by doubling blocks marked with a symbol * in FIG. 4 (gas partial pressure sensor 8, temperature measuring sensor 10, remote switch 21, A/D converter, etc.). With this modification, oxygen partial pressure in arterial blood and that in a biological tissue inside the myocardium can be measured simultaneously. Results of the simultaneous measurements may be recorded on a single recorder 30 or graphic printer 18. If the results of the measurements exceed a predetermined control limit, audible or visual alarm unit 29 may be energized.

For protection of the living body, especially, in the measurement of a human body, the amplifiers 25 and 26 may respectively include isolation amplifier circuits employing a transformer coupling. Further, other lines may also be isolated electrically.

As has been described, the method of the present invention permits accurate and continuous monitoring of gas partial pressure in the living body and can be applied advantageously to clinical and experimental medical treatment.

We claim:

1. An apparatus for measuring a partial pressure of gas in a living body based on the principle of polarography comprising:

a gas partial pressure sensor including a biomedical electrode and a counter electrode for producing an output signal indicative of a polargraphic current, at least said biomedical electrode being placed in said living body wherein said biomedical electrode has a tip end surface covered with a membrane comprised of an outer dense, thin layer having fine pores of an average diameter of 20 Å to 0.7 μm and an inner porous layer, contigous to and integral with the outer layer, having fine pores of an average diameter of 0.7 μm or more, a temperature sensor adapted to be placed at a position suitable for producing an output signal indicative of a temperature of said living body, an interface unit having an A/D converter which digitizes the output signals from said partial pressure sensor and said temperature sensor, an operation unit connected to said interface unit to receive the digitized values of the output signals of said gas partial pressure sensor and said temperature sensor, said operation unit correcting the digitized output signal of said gas partial pressure sensor to an output signal value at a reference temperature on the basis of the temperature measured by said temperature sensor, in accordacne with the following equation:

$$I_t = I_{ST}(k)^{T-t}$$

where $I_t$ is the output value of the gas partial pressure sensor at t° C., $I_{ST}$ is the output value of the gas partial pressure sensor at T° C., k is the temperature coefficient of the gas partial pressure sensor, and t is the temperature measured by the temperature sensor, and calculating a gas partial pressure on the basis of a working curve prepared in said operation unit in advance, said working curve representing a relationship between said gas partial pressure and said corrected digitized output signal of said gas partial pressure sensor.

2. An apparatus for measuring a gas partial pressure according to claim 1 further comprising an alarm unit which is connected to said operation unit and is energized upon receiving a signal from said operation unit representative of that the value of the gas partial pressure corrected by said operation unit has exceeded a preset limit value, for informing thereof to an operator audibly and/or visually.

3. An apparatus for measuring a gas partial pressure according to claim 1 wherein each of said gas partial pressure sensor and temperature sensor is connected to an amplifier having an isolation amplifier circuit in said interface unit.

4. A method for measuring a partial pressure of gas in a living body on the basis of the principle of polarography comprising the steps of:

placing a biomedical electrode, of a gas partial pressure sensor in the living body, a tip end surface of said electrode being covered with a porous membrane comprised of a most outer layer consisting of a thin dense membrane having fine pores of an average diameter of 20Å to 0.7 μm and an inner layer, contigous to and integral with the outer layer, having fine pores of an average diameter of 0.7 μm or more, said gas partial pressure sensor producing an output of a value which is responsive to the gas partial pressure in said living body, placing a temperature sensor at a position suitable to sequentially measure a temperature of said living body, correcting the value of the output signal from said gas partial pressure sensor continously to a value at a reference temperature on the basis of the temperature measured by said temperature sensor, in accordance with the following equation:

$$I_t = I_{ST}(k)^{T-t}$$

where $I_t$ is the output value of the gas partial pressure sensor at t° C., $I_{ST}$ is the output value of the gas partial pressure sensor at T° C., k is the temperature coefficient of the gas partial pressure sensor, and t is the temperature measured by the temperature sensor, and determining a gas partial pressure value of said living body continuously from said corrected output value and a working curve, said working curve being prepared in advance and representing a relationship between the gas partial pressure value and said corrected output value.

5. A method according to claim 4 wherein the value of the output signal from said gas partial pressure sensor is corrected in temperature range of said living body from below 10° C. to over 40° C.

6. A method of measuring a gas partial pressure according to claim 4 wherein the working curve is determined by making the output value of said gas partial pressure sensor related to a gas partial pressure value which is measured in advance.

7. A method of measuring a gas partial pressure according to claim 4 wherein the working curve is determined by placing said gas partial pressure sensor in one kind of test solution having a known gas partial pressure value and by using an output value and a residual current value of said gas partial pressure sensor and the known gas partial pressure value of the test solution.

8. A method of measuring a gas partial pressure according to claim 4 wherein the working curve is determined by placing said gas partial pressure sensor in two kinds of test solutions having known gas partial pressure values and by using output values of said gas partial pressure sensor and the corresponding known gas partial pressure values of the test solutions.

9. A method of measuring a gas partial pressure according to claim 4 wherein said gas partial pressure sensor comprises a biomedical electrode whose tip end surface is covered with a membrane comprises of an outer dense, thin layer having fine pores of an average diameter of 20 Å to 0.7 μm and an inner porous layer, contiguous to and integral with the outer layer, having fine pores of an average diameter of 0.7 μm or more.

* * * * *